(12) United States Patent
Mori et al.

(10) Patent No.: US 7,749,436 B2
(45) Date of Patent: Jul. 6, 2010

(54) GAS INJECTION AMOUNT DETERMINING METHOD IN ISOTOPE GAS ANALYSIS, AND ISOTOPE GAS ANALYZING AND MEASURING METHOD AND APPARATUS

(75) Inventors: Masaaki Mori, Hirakata (JP); Yasuhiro Kubo, Konan (JP); Yasushi Zasu, Kyoto (JP); Masayuki Tani, Hirakata (JP); Tamotsu Hamao, Kyoto (JP)

(73) Assignee: Otsuka Pharmaceutical Co., Ltd., Tokyo (JP)

( * ) Notice: Subject to any disclaimer, the term of this patent is extended or adjusted under 35 U.S.C. 154(b) by 982 days.

(21) Appl. No.: 10/577,451

(22) PCT Filed: Oct. 29, 2004

(86) PCT No.: PCT/JP2004/016451

§ 371 (c)(1),
(2), (4) Date: Apr. 27, 2006

(87) PCT Pub. No.: WO2005/041769

PCT Pub. Date: May 12, 2005

(65) Prior Publication Data

US 2007/0077167 A1    Apr. 5, 2007

(30) Foreign Application Priority Data

Oct. 31, 2003   (JP) .............................. 2003-373093

(51) Int. Cl.
*G01N 33/00* (2006.01)

(52) U.S. Cl. .............................. 422/54; 422/50; 422/83; 422/84; 422/91; 422/93

(58) Field of Classification Search .................... 422/54, 422/50, 83, 84, 91, 93
See application file for complete search history.

(56) References Cited

U.S. PATENT DOCUMENTS 3,437,449 A    4/1969   Luckey (Continued)

FOREIGN PATENT DOCUMENTS

| DE | 196 49 343 | 6/1998 |
|---|---|---|
| DE | 197 31 889 | 1/1999 |
| DE | 197 50 133 | 7/1999 |
| JP | 55-112546 | 8/1980 |
| JP | 59-171836 | 9/1984 |

(Continued)

OTHER PUBLICATIONS

S. Tetsyo, "13C Exhalation Gas Inspecting System,"Patent Abstracts of Japan, vol. 96, No. 006 (1996).

(Continued)

*Primary Examiner*—Sam P Siefke
(74) *Attorney, Agent, or Firm*—Finnegan, Henderson, Farabow, Garrett & Dunner, L.L.P.

(57) ABSTRACT

As previous processing of measurement in which gas to be measured containing, as gas components, carbon dioxide $^{13}CO_2$ and carbon dioxide $^{12}CO_2$, is introduced into a cell, and in which the intensities of transmitted lights having wavelengths suitable for measurement of the respective gas components, are measured and then data-processed to measure the concentrations of the gas components, the air having a predetermined volume Va is sucked by a gas injection device 21, a gas exhaust valve V6 of a cell 11 is closed and the air stored in the gas injection device 21 is transferred to the cell 11 filled with the air at an atmospheric pressure, thereby to pressurize the cell inside. The pressure thus pressurized is measured as P. The cell volume Vc is subtracted from the product obtained by multiplying the sum. V0 of the volume Va and Vc the cell volume Vc, by the ratio P0/P in which P0 is the target pressure of the gas to be measured at which a calibration curve has been prepared for an isotope gas analysis and measurement, thus determining the one-time gas injection amount of the gas injection device 21. Thus, measured concentration variations based on changes in atmospheric pressure can be corrected.

7 Claims, 6 Drawing Sheets

U.S. PATENT DOCUMENTS

| | | | |
|---|---|---|---|
| 3,544,273 | A | 12/1970 | McConnaughey |
| 3,734,692 | A | 5/1973 | Lucker et al. |
| 4,232,223 | A | 11/1980 | Ohnishi et al. |
| 4,247,773 | A | 1/1981 | Nexo et al. |
| 4,256,964 | A | 3/1981 | Ishida et al. |
| 4,499,377 | A | 2/1985 | Presser |
| 4,829,183 | A | 5/1989 | McClatchie et al. |
| 4,937,448 | A | 6/1990 | Mantz et al. |
| 5,131,387 | A | 7/1992 | French et al. |
| 5,146,294 | A | 9/1992 | Grisar et al. |
| 5,479,019 | A | 12/1995 | Gross |
| 5,486,699 | A | 1/1996 | Fabinski et al. |
| 5,543,621 | A | 8/1996 | Sauke et al. |
| 5,591,975 | A | 1/1997 | Jack et al. |
| 5,747,809 | A | 5/1998 | Eckstrom |
| 5,964,712 | A | 10/1999 | Kubo et al. |
| 6,002,133 | A | 12/1999 | Nelson et al. |
| 6,274,870 | B1 | 8/2001 | Kubo et al. |
| 6,444,985 | B1 | 9/2002 | Mori et al. |
| 6,455,852 | B2 | 9/2002 | Mori et al. |
| 6,940,083 | B2 | 9/2005 | Mori et al. |
| 2001/0021815 | A1 | 9/2001 | Katzman et al. |
| 2002/0011569 | A1 | 1/2002 | Mori et al. |
| 2002/0134940 | A1 | 9/2002 | Ohkubo et al. |
| 2003/0178589 | A1 | 9/2003 | Mori et al. |

FOREIGN PATENT DOCUMENTS

| | | |
|---|---|---|
| JP | 3-31218 | 11/1984 |
| JP | 61-011634 | 1/1986 |
| JP | 61-42219 | 9/1986 |
| JP | 62-261032 | 11/1987 |
| JP | 2-42338 | 2/1990 |
| JP | 4-160349 | 6/1992 |
| JP | 4-364442 | 12/1992 |
| JP | 5-142146 | 6/1993 |
| JP | 5-296922 | 11/1993 |
| JP | 7-190930 | 7/1995 |
| JP | 10-197433 | 7/1998 |
| JP | 3014652 | 12/1999 |
| JP | 3176302 | 4/2001 |
| TW | 421713 B | 2/2001 |
| TW | 542910 B | 7/2003 |
| WO | WO 93/06460 | 4/1993 |
| WO | WO 98/30888 | 7/1998 |
| WO | WO 99/12471 | 3/1999 |
| WO | WO 02/25250 | 3/2002 |

OTHER PUBLICATIONS

K. Nobuhiko, "Method and Device for Collecting Exhalation," Patent Abstracts of Japan, vol. 96, No. 10 (1996).

K. Kouichi, "Method and Equipment for Measuring 13 C02," Patent Abstracts of Japan, vol. 10, No. 157, Jan. 1986.

GAS INJECTION AMOUNT DETERMINING METHOD IN ISOTOPE GAS ANALYSIS, AND ISOTOPE GAS ANALYZING AND MEASURING METHOD AND APPARATUS

BACKGROUND OF THE INVENTION

1. Field of the Invention

After a medicine containing isotopes has been administered to a living body, the metabolic rate of the living body can be measured by measuring changes in concentration ratio of the isotopes. Accordingly, isotope analysis is utilized for disease diagnosis in the medical field.

The present invention is achieved with attention focused on the difference in light absorption characteristics of isotopes, and relates to a gas injection amount determining method in isotope gas analysis for measuring the concentration ratio of isotope gases, and also relates to isotope gas analyzing and measuring method and apparatus.

2. Description of Related Art

It is generally known that bacteria called *Helicobacter pylori* (HP) are present in the stomach as the cause of gastric ulcer and gastritis.

When HP is present in the patient's stomach, it is required to conduct a bacteria elimination treatment by administering an antibiotic substance. Accordingly, it is important whether or not HP is present in the patient. HP presents a strong urease activity and therefore dissolves urea into carbon dioxide and ammonia.

On the other hand, carbon includes isotopes of which mass number is 13 and 14, in addition to 12. Out of these isotopes, the isotope $^{13}C$ having the mass number of 13 is not radioactive and is sable, thus causing the same to be readily handled.

In this connection, when urea marked with the isotope $^{13}C$ is administered to a living body (patient), and the $^{13}C$ concentration, more specifically the concentration ratio between $^{13}CO_2$ and $^{12}CO_2$, in the expired breath of the patient which is the final metabolic product, is measured, the presence/absence of HP can be made sure.

However, the concentration ratio between $^{13}CO_2$ and $^{12}CO_2$ in the natural world, is as high as 1:100. It is therefore difficult to precisely measure the concentration ratio in the expired breath of the patient.

Conventionally, it is known a method using infrared spectral diffraction as a method of obtaining the concentration ratio between $^{13}CO_2$ and $^{12}CO_2$ or the concentration of $^{13}CO_2$ (See Japanese Patent Publication No. 61(1986)-42220(B)).

According to the method of Japanese Patent Publication No. 61(1986)-42220(B), there are prepared two, long and short, cells having lengths such that the $^{12}CO_2$ absorption in one cell is equal to the $^{13}CO_2$ absorption in the other cell, and lights having wavelengths suitable for respective analyses are irradiated to the respective cells, and the intensities of the transmitted lights are measured. According to this method, the light absorption ratio at the concentration ratio in the natural field can be made 1, and if the concentration ratio undergoes a change, the light absorption ratio varies according to this change. Thus, the change in concentration ratio can be known.

Even though there is adopted the method using infrared spectral diffraction above-mentioned, it is difficult to detect a slight change in concentration ratio.

According to the isotope gas analyzing and measuring method above-mentioned, the concentration of carbon dioxide $^{13}CO_2$ is obtained with the use of a calibration curve which determines the relationship between absorbance and concentration of $^{13}CO_2$. However, if the atmospheric pressure at which the calibration curve has been prepared, is different from the atmospheric pressure at which the absorbance of carbon dioxide $^{13}CO_2$ is measured, such difference may cause an error of measurement of $^{13}CO_2$ concentration.

Table 1 shows the results of measurement of $CO_2$ concentration obtained in the following manner. That is, a predetermined volume of air having a predetermined $CO_2$ concentration, was collected by a gas injection device at each of a plurality of atmospheric pressures, and was then injected into a cell. Each cell inside pressure was measured. Then, each absorbance was measured to measure the $CO_2$ concentration. The calibration curve used at this time was prepared at an atmospheric pressure of 1005 hPa.

TABLE 1

| Atmospheric Pressure (hPa) | Cell Pressure (Mpa) | $CO_2$ Concentration |
|---|---|---|
| 1005 | 0.402 | 2.995 |
| 964 | 0.385 | 2.874 |
| 892 | 0.357 | 2.536 |
| 858 | 0.347 | 2.445 |
| 799 | 0.323 | 2.245 |

According to Table 1, the cell inside pressures are naturally proportional to the atmospheric pressures, and the $CO_2$ concentrations which must originally be constant, are lowered according to the reduction in atmospheric pressure. Thus, the concentration varies with the variations of the atmospheric pressure.

In measurement in which gas to be measured containing, as gas components, carbon dioxide $^{13}CO_2$ and carbon dioxide $^{12}CO_2$, is introduced into a cell, and in which the intensities of transmitted lights having wavelengths suitable for measurement of the respective gas components, are measured and then data-processed to measure the concentrations of the gas components, it is an object of the present invention to provide a gas injection amount determining method in isotope gas analysis, and isotope gas analyzing/measuring method and apparatus, each of which can correct concentration variations resulting from the atmospheric pressure variations, thus improving the measuring precision.

SUMMARY OF THE INVENTION

According to the present invention, a gas injection amount determining method in isotope gas analysis comprises the steps of: filling a cell with the air at an atmospheric pressure; operating a gas injection device so as to suck the air of a predetermined volume Va, the gas injection device being arranged to inject the gas to be measured into the cell; transferring the air stored in the gas injection device into the cell to pressurize the cell inside, and measuring the cell inside pressure P; and subtracting the cell volume Vc from the product obtained by multiplying the sum V0 of the volume Va and the cell volume Vc, by the ratio P0/P in which P0 is the target pressure of the gas to be measured in isotope gas analysis measurement, thus determining the one-time gas injection amount of the gas injection device.

According to the method above-mentioned, when an isotope gas analysis measurement is conducted with the use of the one-time gas injection amount determined by multiplying the ratio P0/P with the standard volume or sum V0 of the volume Va and the cell volume Vc, the gas to be measured can be measured at the target pressure P0 of the gas to be measured. In other words, the cell inside pressure influenced by variations of the atmospheric pressure can be corrected.

Accordingly, the measuring precision and the reproducibility are improved. Further, the measuring apparatus is not required to be made in large sizes.

It is preferable that the cell volume Vc includes not only net volume of the cell, but also inner volumes of pipes, valves and pressure sensor which are in connection through the cell. With use of the above volume Vc, more precise measurement can be attained.

The target pressure P0 of the gas to be measured is preferably equal to the gas pressure at which a calibration curve for determining the relationship between absorbance and concentration of carbon dioxide $^{13}CO_2$, has been prepared.

According to an isotope gas analyzing and measuring method of the present invention, gas to be measured having the volume determined by the gas injection amount determining method above-mentioned, is collected by a gas injection device, the gas thus collected is transferred into the cell to pressurize the cell inside, and the concentration of the carbon dioxide $^{13}CO_2$ or the concentration ratio $^{13}CO_2/^{12}CO_2$ is measured.

An isotope gas analyzing and measuring apparatus of the present invention is arranged to embody the isotope gas analyzing and measuring method above-mentioned, and comprises: a gas injection device for injecting gas into a cell; gas transferring means for transferring the gas stored in the gas injection device into the cell; a pressure sensor for measuring the pressure of the gas housed in the cell; and gas injection amount determining means arranged such that the air having a predetermined volume Va is sucked by the gas injection device, that the air stored in the gas injection device is transferred to the cell filled with the air at an atmospheric pressure, thereby to pressurize the cell inside, that the cell inside pressure P is measured, and that the cell volume Vc is subtracted from the product obtained by multiplying the sum V0 of the volume Va and the cell volume Vc, by the ratio P0/P in which P0 is the target pressure of the gas to be measured in isotope gas analysis measurement, thus determining the one-time gas injection amount of the gas injection device; whereby gas to be measured having the volume determined by the gas injection amount determining means, is collected by the gas injection device, the gas thus collected is transferred into the cell filled with gas to be measured at an atmospheric pressure, and the concentration of carbon dioxide $^{13}CO_2$ or the concentration ratio $^{13}CO_2/^{12}CO_2$ is measured.

DESCRIPTION OF THE PREFERRED EMBODIMENTS

Referring to the attached drawings, the following description will discuss in detail an embodiment of the present invention in which after a urea diagnostic medicine marked with an isotope $^{13}C$ has been administered to a living body, the $^{13}CO_2$ concentration of an expired breath of the living body is spectroscopically measured.

I. Expired Breath Test

First, an expired breath of a patient before a urea diagnostic medicine is administered, is collected in an expired breath bag. Then, a urea diagnostic medicine is orally administered to the patient. After the passage of about 20 minutes, an expired breath is collected in an expired breath bag in a manner similar to that before administration.

The expired breath bags before and after administration are respectively set to predetermined nozzles of an isotope gas spectroscopic measurement apparatus. Then, the following automatic measurement is conducted.

II. Isotope Gas Spectroscopic Measurement Apparatus

Figure 1:
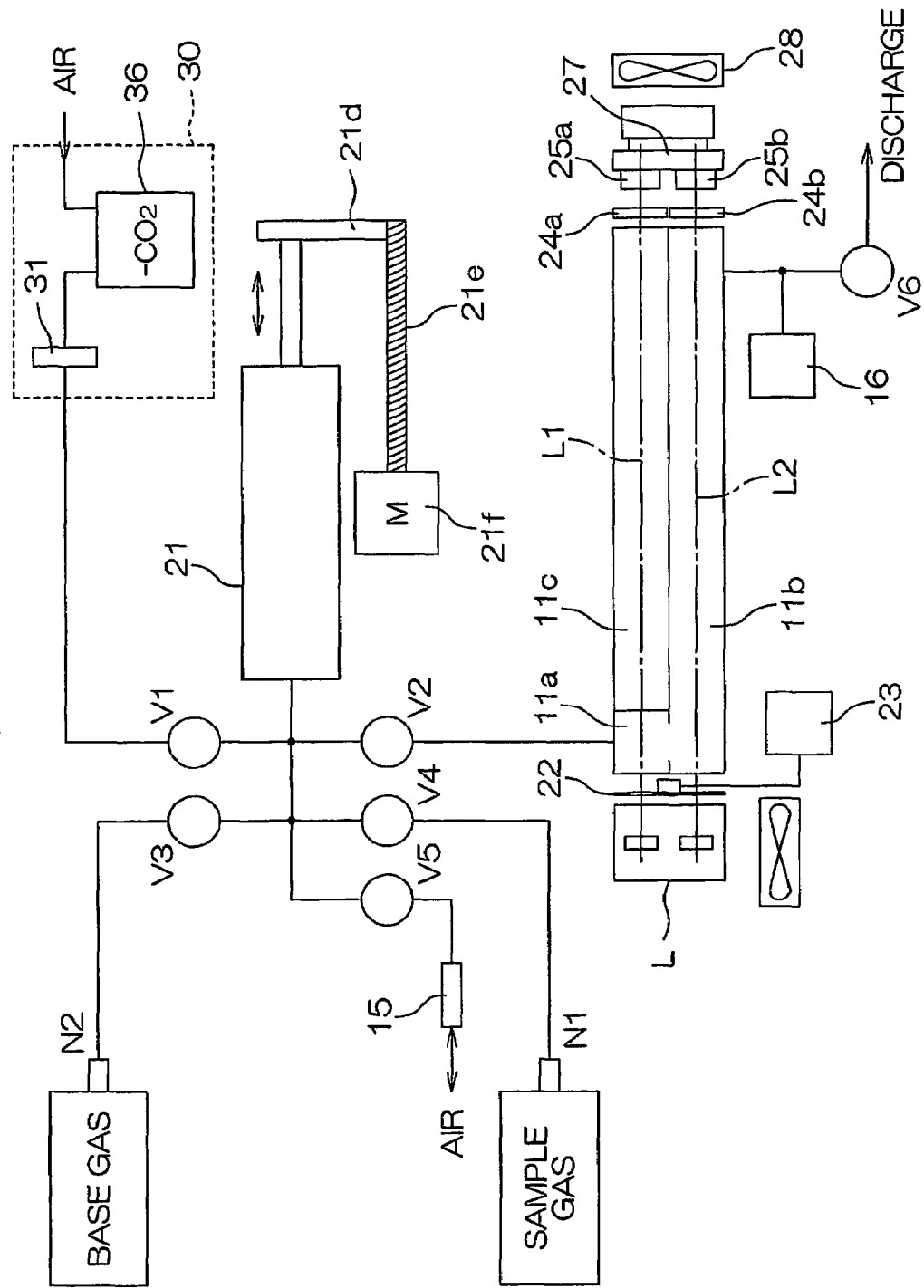
FIG. 1 is a block diagram illustrating the general arrangement of an isotope gas spectroscopic measurement apparatus.

FIG. 1 is a block diagram illustrating the general arrangement of an isotope gas spectroscopic measurement apparatus.

The expired breath bag containing the expired breath after administration (hereinafter referred to as "sample gas"), and the expired breath bag containing the expired breath before administration (hereinafter referred to as "base gas"), are respectively set to nozzles N1 and N2. The nozzle N1 is connected to an electromagnetic valve (hereinafter simply referred to as "valve") V4 through a metallic pipe (hereinafter simply referred to as "pipe"). The nozzle N2 is connected to a valve V3 through a pipe. A valve V5 is connected to a pipe for taking in the air through a dust-proof filter 15.

On the other hand, a reference gas (In this embodiment, the air with $CO_2$ removed is used) supplied from a reference gas supply unit 30 (to be discussed later), is supplied to a valve V1.

The valves V1, V3, V4 and V5 are connected to the gas injection device 21 for quantitatively injecting a reference gas, a sample gas or a base gas. The gas injection device 21 has a syringe shape having a piston and a cylinder. The piston is driven by a feed screw 21e connected to a pulse motor 21f in association with a nut 2d fixed to the piston (to be discussed later). The maximum gas injection amount of the gas injection device 21 is 40 ml.

The gas injection device 21 is connected, through a valve V2, to a first sample cell 11a and a second sample cell 11b.

As shown in FIG. 1, the cell chamber 11 has the short first sample cell 11a for measuring the $^{12}CO_2$ absorption, the long second sample cell 11b for measuring the $^{13}CO_2$ absorption, and a dummy cell 11c containing gas which is not absorbed in the $CO_2$ absorbing range. Provision is made such that the first sample cell 11a and the second sample cell 11b communicate with each other, and that gas introduced into the first sample cell 11a enters, as it is, the second sample cell 11b, and is then discharged through an exhaust valve V6.

Disposed upstream of the exhaust valve V6 is a pressure sensor 16 for measuring the gas pressure in the first sample cell 11a and the second sample cell 11b. No restrictions are imposed on the detection method of this pressure sensor 16, but there may be used for example a pressure sensor of the type in which the movement of a diaphragm is detected by a piezoelectric element.

The first sample cell 11a has a capacity of about 0.085 ml, while the second sample cell 11b has a capacity of about 3.96 ml. More specifically, the first sample cell 11a has a length of 3 mm, the second sample cell 11b has a length of 140 mm, and the dummy cell 11c has a length of 135 mm. The cell chamber 11 is surrounded by an insulating material (not shown).

There is also disposed an infrared light source device L having two light sources for irradiating infrared rays. Infrared rays may be generated by an optional method. For example, there may be used a ceramics heater (surface temperature of 700° C.) or the like. There is further disposed a chopper 22 for interrupting and passing infrared rays at predetermined intervals. The chopper 22 is rotated by a pulse motor 23.

Out of the infrared rays irradiated from the infrared light source device L, the light path formed by infrared rays passing through the first sample cell 11a and the dummy cell 11c, is called a first light path L1, and the light path formed by infrared rays passing through the second sample cell 11b, is called a second light path L2 (See FIG. 1).

An infrared rays detector device for detecting the infrared rays having passed through the cells comprises: a first wavelength filter 24a and a first sensor element 25a disposed in the first light path; and a second wavelength filter 24b and a second sensor element 25b disposed in the second light path.

For measuring the absorption of $^{12}CO_2$, the first wavelength filter 24a is designed to pass infrared rays having a wavelength of about 4280 nm which is the $^{12}CO_2$ absorption wavelength range. For measuring the absorption of $^{13}CO_2$, the second wavelength filter 24b is designed to pass infrared rays having a wavelength of about 4412 nm which is the $^{13}CO_2$ absorption wavelength range. The first and second sensor elements 25a, 25b are light-receiving elements for detecting infrared rays.

The first wavelength filter 24a, the first sensor element 25a, the second wavelength filter 24b, and the second sensor element 25b are maintained at a predetermined temperature by a temperature controlling block 27.

A fan 28 is disposed for discharging, to the outside of the apparatus, heat radiated from a Peltier element of the temperature controlling block 27.

Further, the isotope gas spectroscopic measurement apparatus has a reference gas supply unit 30 for supplying the air with $CO_2$ removed. The reference gas supply unit 30 is connected in series to a dust-proof filter 31 and a carbonic acid gas absorbing unit 36.

The carbonic acid gas absorbing unit 36 is arranged to use for example soda lime (a mixture of sodium hydroxide and calcium hydroxide), as a carbonic acid gas absorbing agent.

Figure 2A:
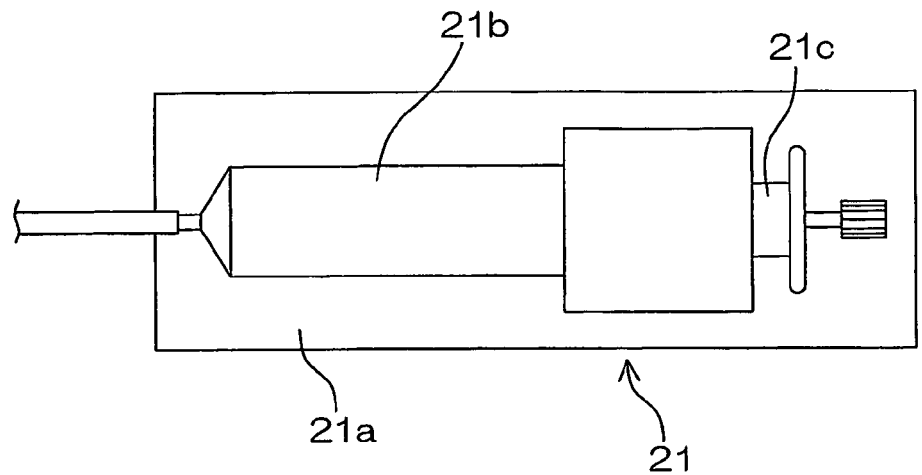
FIG. 2(a) is a plan view of a gas injection device 21 for quantitatively injecting gas to be measured.
Figure 2B:
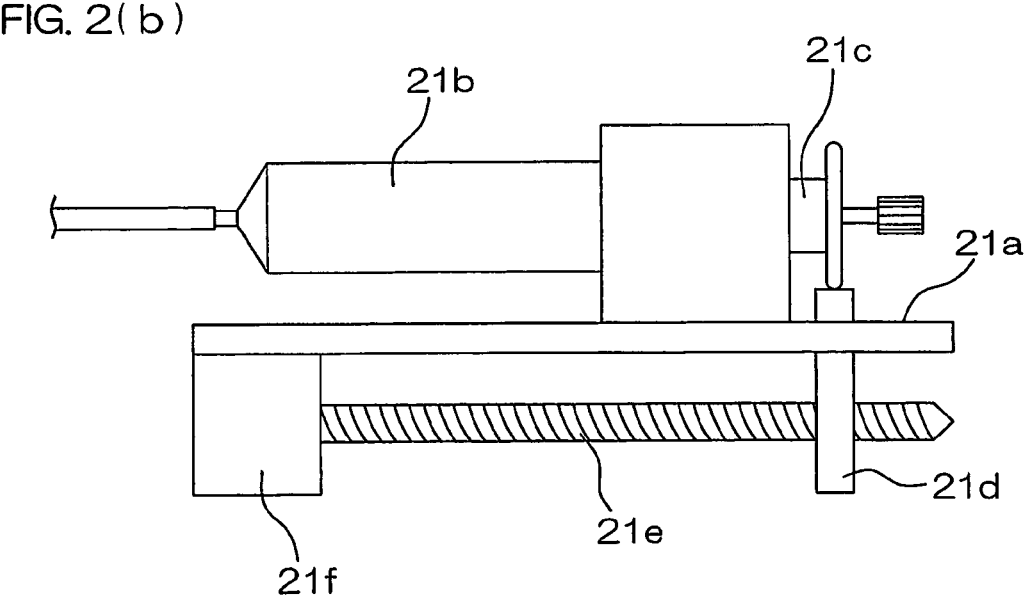
FIG. 2(b) is a front view of the gas injection device 21.

FIG. 2(a) is a plan view of a gas injection device 21 for quantitatively injecting gas to be measured, and FIG. 2(b) is a front view of the gas injection device 21.

The gas injection device 21 has a base stand 21a, a cylinder 21b having a piston 21c disposed on the base stand 21a, a movable nut 21d coupled to the piston 21c, a feed screw 21e meshed with the nut 21d, and a pulse motor 21f for rotating the feed screw 21e, the nut 21d, the feed screw 21e and the pulse motor 21f being disposed under the base stand 21a.

The pulse motor 21f is driven forwardly/reversely by a driving circuit (not shown). When the feed screw 21e is rotated by the rotation of the pulse motor 21f, the nut 21d is moved back and forth according to the rotation direction. This causes the piston 21c to be moved back and forth to an optional position. It is therefore possible to optionally control both the introduction of gas to be measured, into the cylinder 21b, and the discharge of the gas to be measured from the cylinder 21b.

III. Measuring Procedure

The measuring process comprises the steps of determining a one-time gas injection amount, measuring the reference gas, measuring the base gas, measuring the reference gas, measuring the sample gas, and measuring the reference gas and the like. In FIGS. 3 to 5, the arrows show the gas flowing.

III-1. Determination of the One-Time Gas Injection Amount

This gas injection amount determining step may be conducted at each measurement of a sample gas or at regular time intervals (e.g., every one hour).

It is now supposed that the total of the first sample cell 11a volume and the second sample cell 11b volume is defined as Vc (a predetermined value). The volume Vc preferably not only includes the net volume of the sample cells 11a, 11b, but also includes inner volumes of the pipes, valves and pressure sensor 16 which are connected through the sample cells 11a, 11b. It is also supposed that the volume of the gas injection device 21 at the time when gas is injected by the gas injection device 21 to a predetermined scale thereof, is defined as Va. It is supposed that Vc+Va=V0. This volume V0 is defined as a standard volume V0.

The valve V5 is opened, other valves are closed, and the air is sucked with the use of the gas injection device 21. Then, the valve V5 is closed, and the valve V2 and the exhaust valve V6 are opened. The air in the gas injection device 21 is injected into the first sample cell 11a and the second sample cell 11b. Then, the valve V2 is closed and the exhaust valve V6 is closed. Thus, the air having the volume Vc at the atmospheric pressure is housed in the first sample cell 11a and the second sample cell 11b.

Figure 3A:
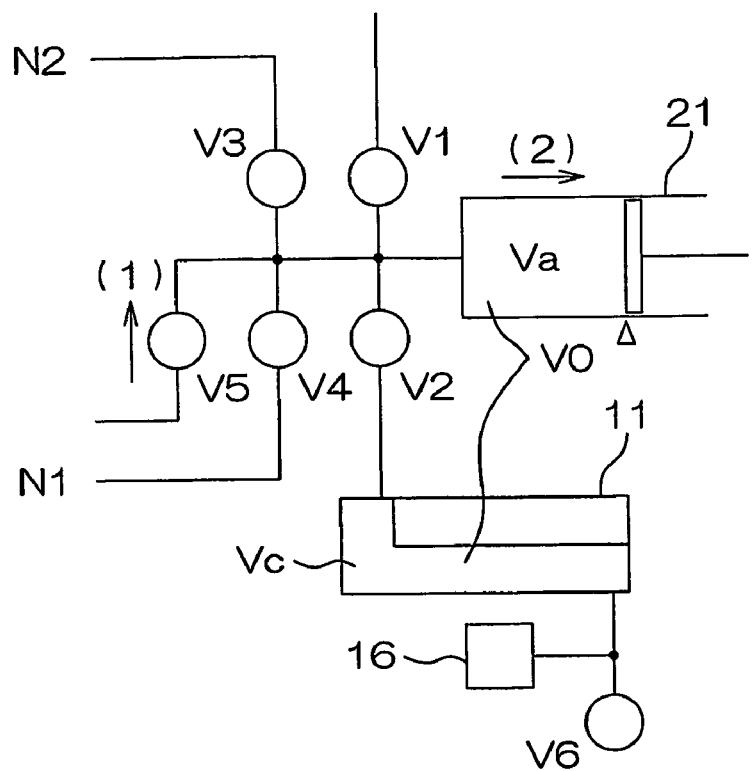
FIG. 3(a) and FIG. 3(b) are views illustrating gas flow passages at the time when a one-time gas injection amount is determined.

As shown in FIG. 3(a), the valve V5 is opened, other valves are closed, and the air of volume Va is sucked with the use of the gas injection device 21.

Figure 3B:
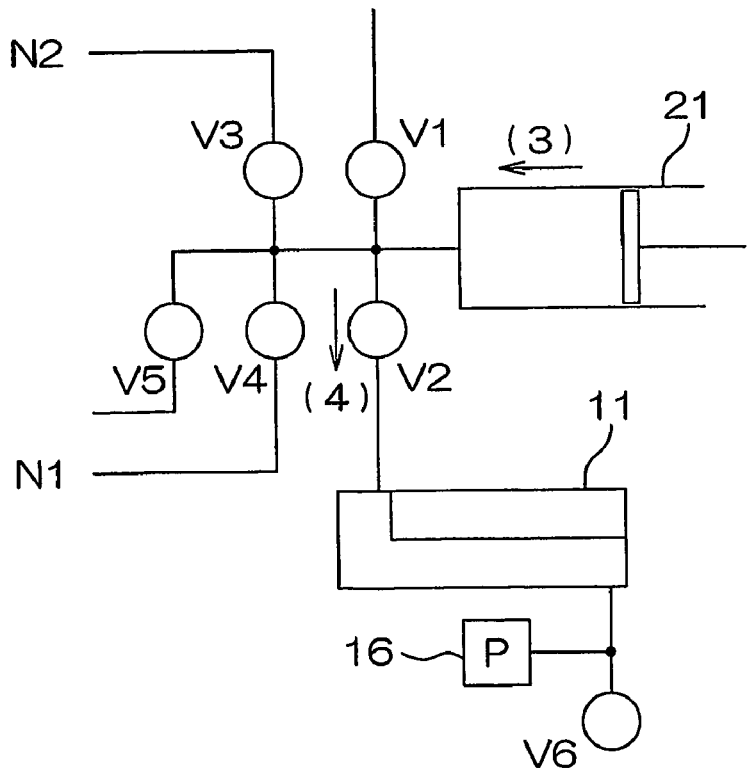

As shown in FIG. 3(b), the valve V5 is closed and the valve V2 is opened to transfer the air in the gas injection device 21 into the first sample cell 11a and the second sample cell 11b. Since the exhaust valve V6 remains closed, the insides of the first sample cell 11a and the second sample cell 11b are pressurized.

With the valve V2 closed to stop the air movement, the pressure of the first sample cell 11a and the second sample cell 11b is measured by the pressure sensor 16. This measured pressure value is defined as P.

It is supposed that each calibration curve for determining the relationship between absorbance and concentration of each of carbon dioxide $^{13}CO_2$ and carbon dioxide $^{12}CO_2$, has been prepared at a predetermined pressure P0 (i.e., 4 atmospheric pressure). The calibration curve data and the value of the predetermined pressure P0 are stored in an analysis computer of the isotope gas spectroscopic measurement apparatus.

The analysis computer determines a one-time measuring gas volume V0 (P0/P) with the use of the previously stored pressure P0, the measured pressure P and the standard volume V0. As shown by the following equation 1), the gas injection amount V of the gas injection device 21 is a value obtained by subtracting the cell volume Vc from V0 (P0/P). In the equation (1), the volume Vc is subtracted because the first sample cell 11a and the second sample cell 11b already contain the gas to be measured having the volume Vc.

$$V = V0(P0/P) - Vc \tag{1}$$

The following description will discuss the equation (1). When the measured pressure P is equal to p0, the gas injection amount V is equal to Va. If the atmospheric pressure is high, the measured pressure P is higher than P0. At this time, the gas injection amount V may be set to a value smaller than Va. If the atmospheric pressure is low, the measured pressure P is lower than P0. At this time, the gas injection amount V maybe set to a value higher than Va. With such an operation, the $CO_2$ concentration can always be measured under conditions identical to those under which the calibration curve has been prepared.

III-2. Reference Measurement

A clean reference gas is flowed into the gas flow passages and the cell chamber 11 of the isotope gas spectroscopic measurement apparatus to wash the gas flow passages and the cell chamber 11. At this time, the piston 21c is moved back and forth to wash the inside of the cylinder 21b. A reference gas at an atmospheric pressure is housed in the first sample cell 11a and the second sample cell 11b.

Figure 4A:
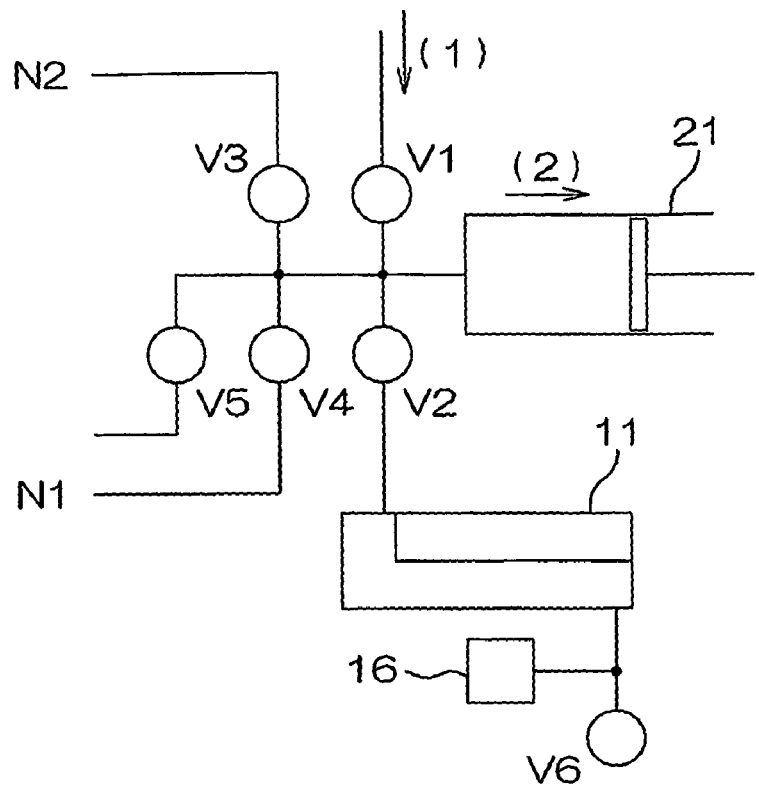
FIG. 4(a) and FIG. 4(b) are views illustrating gas flow passages at the time when a reference gas light amount measurement is conducted.

In the reference measurement, the valve V1 is opened, other valves are closed, and a reference gas is sucked with the use of the gas injection device 21, as shown in FIG. 4(a).

Figure 4B:
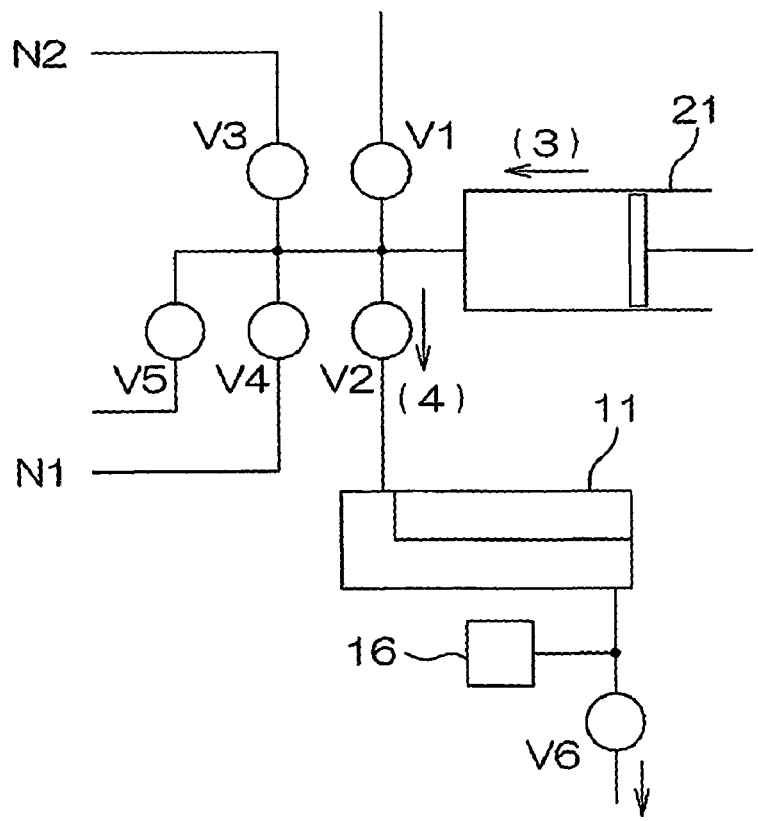

Then, as shown in FIG. 4(b), the valve V1 is closed, and the valve V2 and the exhaust valve V6 are opened. While the reference gas in the gas injection device 21 is slowly flowed into the first sample cell 11a and the second sample cell 11b by controlling the gas injection device 21, the light amount measurement is conducted by the sensor elements 25a, 25b.

The light amount thus obtained by the first sensor element 25a is recorded as $^{12}R1$, and the light amount thus obtained by the second sensor element 25b is recorded as $^{13}R1$.

III-3. Base Gas Measurement

The valve V3 is opened, other valves are closed and the base gas is sucked with the use of the gas injection device 21. Then, the valve V3 is closed, the valve V2 and the exhaust valve V6 are opened, and the base gas in the gas injection device 21 is injected into the first sample cell 11a and the second sample cell 11b. Thereafter, the exhaust valve V6 is closed. Thus, the base gas at an atmospheric pressure is housed in the first sample cell 11a and the second sample cell 11b.

Figure 5A:
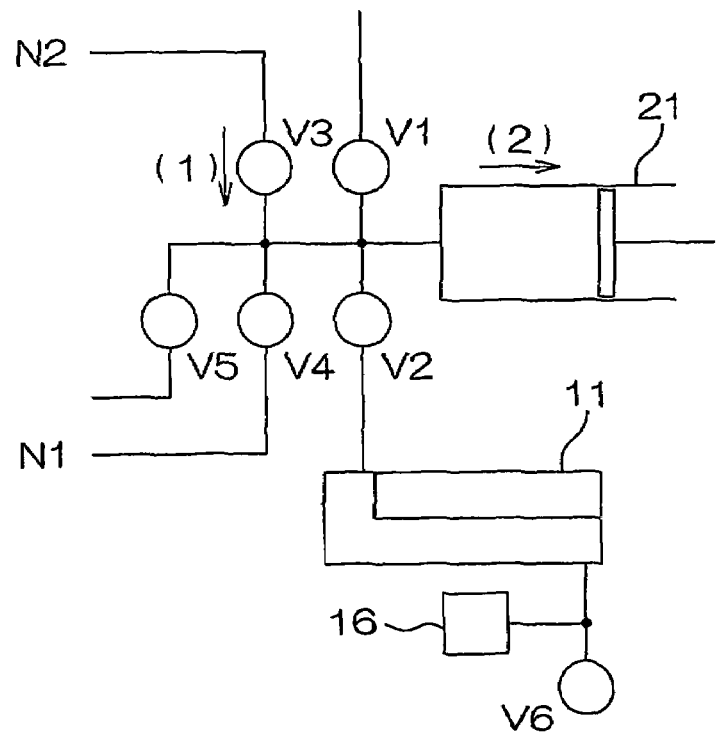
FIG. 5(a) and FIG. 5(b) are view illustrating gas flow passages at the time when a base gas light amount measurement is conducted.

Then, the valve V3 is opened, other valves are closed and the base gas having the volume V calculated according to the equation (1) is sucked from the expired breath bag by the gas injection device 21, as shown in FIG. 5(a).

Figure 5B:
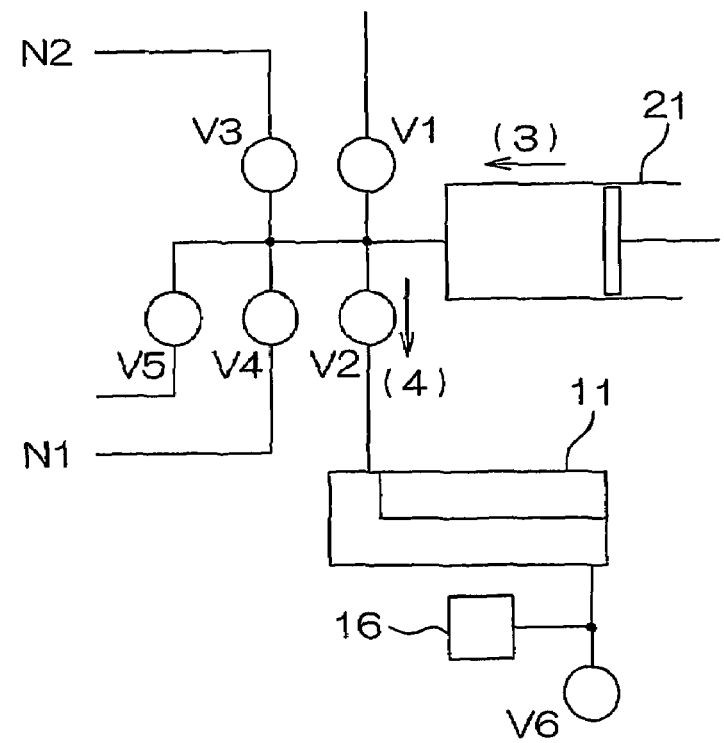

After the base gas has been sucked, the valve V3 is closed, and the valve V2 is opened as shown in FIG. 5(b). The base gas is mechanically pushed out with the use of the gas injection device 21 to pressurize the first sample cell 11a and the second sample cell 11b. This increases the pressure of the base gas in the first sample cell 11a and the second sample cell 11b, to a value equal to the pressure P0.

At this state, the valve V2 is closed and the light amount is measured by the sensor elements 25a, 25b.

The light amount thus obtained by the first sensor element 25a is recorded as $^{12}B$, and the light amount thus obtained by the second sensor element 25b is recorded as $^{13}B$.

III-4 Reference Measurement

Again, the gas flow passages and the cells are washed, and the reference gas light amount measurement is conducted (See FIGS. 4 (a), (b)). The light amount thus obtained by the first sensor element 25a is recorded as $^{12}R2$, and the light amount thus obtained by the second sensor element 25b is recorded as $^{13}R2$.

III-5 Sample Gas Measurement

The valve V4 is opened, other valves are closed and the sample gas is sucked with the use of the gas injection device 21. Then, the valve V4 is closed, the valve V2 and the exhaust valve V6 are opened, and the sample gas in the gas injection device 21 is injected into the first sample cell 11a and the second sample cell 11b. Thereafter, the exhaust valve V6 is closed. Thus, the sample gas at an atmospheric pressure is housed in the first sample cell 11a and the second sample cell 11b.

Figure 6A:
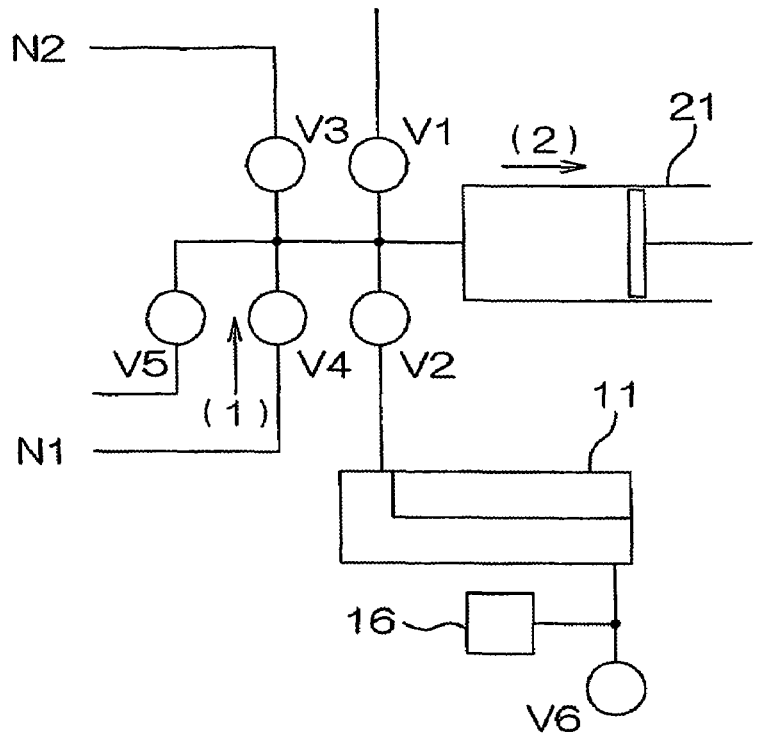
FIG. 6(a) and FIG. 6(b) are view illustrating gas flow passages at the time when a sample gas light amount measurement is conducted.

Then, the valve V4 is opened, other valves are closed and the sample gas having the volume V calculated according to the equation (1) is sucked from the expired breath bag by the gas injection device 21, as shown in FIG. 6(a).

Figure 6B:
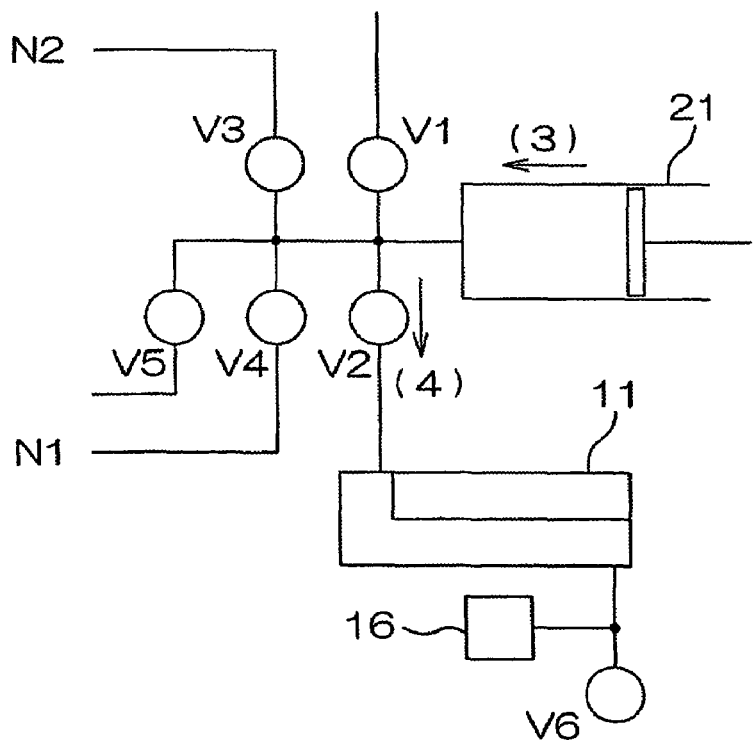

After the sample gas has been sucked, the valve V4 is closed, and the valve V2 is opened, as shown in FIG. 6(b). The sample gas is mechanically pushed out with the use of the gas injection device 21 to pressurize the first sample cell 11a and the second sample cell 11b. This increases the pressure of the sample gas in the first sample cell 11a and the second sample cell 11b, to a value equal to the pressure P0.

At this state, the valve V2 is closed and the light amount is measured by the sensor elements 25a, 25b.

The light amount thus obtained by the first sensor element 25a is recorded as $^{12}S$, and the light amount thus obtained by the second sensor element 25b is recorded as $^{13}S$.

III-6. Reference Measurement

Again, the gas flow passages and the cells are washed, and the reference gas light amount measurement is conducted (See FIGS. 4 (a), (b)).

The light amount thus obtained by the first sensor element 25a is recorded as $^{12}R3$, and the light amount thus obtained by the second sensor element 25b is recorded as $^{13}R3$.

IV Data Processing

IV-1. Calculation of the Base Gas Absorbance Data

First, both the absorbance $^{12}Abs(B)$ of $^{12}CO_2$ and the absorbance $^{13}Abs(B)$ of $^{13}CO_2$ in the base gas, are obtained with the use of (i) the transmitted light amounts $^{12}R1$, $^{13}R1$ of the reference gas, (ii) the transmitted light amounts $^{12}B$, $^{13}B$ of the base gas, and (iii) the transmitted light amounts $^{12}R2$, $^{13}R2$ of the reference gas.

Here, the absorbance $^{12}Abs(B)$ of $^{12}CO_2$ is obtained by the following equation:

$$^{12}Abs(B) = -\log[2\,^{12}B/(^{12}R1 + ^{12}R2)]$$

The absorbance $^{13}Abs(B)$ of $^{13}CO_2$ is obtained by the following equation:

$$^{13}Abs(B) = -\log[2\,^{13}B/(^{13}R1 + ^{13}R2)]$$

Thus, when calculating each absorbance, there is calculated the average value (R1+R2)/2 of the light amounts of reference measurements conducted before and after the absorbance calculation, and the absorbance is then calculated with the use of the average value thus obtained and the light amount obtained by the base gas measurement. Accordingly, the influence of drift (influence exerted to measurement by the passage of time) can be cancelled each other. Accordingly, the measurement can quickly be initiated without the need of waiting until the apparatus is brought into perfect thermal equilibrium after the apparatus has been stared (generally, several hours are required).

IV-2. Calculation of Sample Gas Absorbance Data

Then, both the absorbance $^{12}Abs(S)$ of $^{12}CO_2$ and the absorbance $^{13}Abs(S)$ of $^{13}CO_2$ in the sample gas are obtained with the use of (i) the transmitted light amounts $^{12}R2$, $^{13}R2$ of the reference gas, (ii) the transmitted light amounts $^{12}S$, $^{13}S$ of the sample gas, and (iii) the transmitted light amounts $^{12}R3$, $^{13}R3$ of the reference gas.

Here, the absorbance $^{12}Abs(S)$ of $^{12}CO_2$ is obtained by the following equation:

$$^{12}Abs(S) = -\log[2\,^{12}S/(^{12}R2 + ^{12}R3)]$$

The absorbance $^{13}Abs(S)$ of $^{13}CO_2$ is obtained by the following equation:

$$^{13}Abs(S) = -\log[2\,^{13}S/(^{13}R2 + ^{13}R3)]$$

Thus, when calculating an absorbance, there is calculated the average value of the light amounts of reference measurements conducted before and after the absorbance calculation, and the absorbance is then calculated with the use of the average value thus obtained and the light amount obtained by the sample gas measurement. Accordingly, the influence of drift can be cancelled each other.

IV-3 Concentration Calculation $^{12}CO_2$ concentration and $^{13}CO_2$ concentration are obtained with the use of calibration curves.

As mentioned earlier, the concentration curves are prepared with the use of gas to be measured of which $^{12}CO_2$ concentration is known and gas to be measured of which $^{13}CO_2$ concentration is known.

To obtain the calibration curve for $^{12}CO_2$ concentration, $^{12}CO_2$ absorbance data are measured with the $^{12}CO_2$ concentration changed in the range of 0% to about 8%, and the data thus measured are plotted on a graph in which the axis of abscissas represents the $^{12}CO_2$ concentration and the axis of ordinates represents the $^{12}CO_2$ absorbance. Then, the curve is determined by the method of least squares.

To obtain the calibration curve for $^{13}CO_2$ concentration, $^{13}CO_2$ absorbance data are measured with the $^{13}CO_2$ concentration changed in the range of 0% to about 0.08%, and the data thus measured are plotted on a graph in which the axis of abscissas represents the $^{13}CO_2$ concentration and the axis of ordinates represents the $^{13}CO_2$ absorbance. Then, the curve is determined by the method of least squares.

The curves approximated by quadratic equations are relatively less in error. Accordingly, the calibration curves approximated by quadratic equations are adopted in this embodiment.

There are recorded the $^{12}CO_2$ concentration of the base gas as $^{12}Conc(B)$, the $^{13}CO_2$ concentration of the base gas as $^{13}Conc(B)$, the $^{12}C_2$ concentration of the sample gas as $^{13}Conc(S)$, and the $^{13}CO_2$ concentration of the sample gas as $^{13}Conc(S)$, these concentration data being obtained with the use of the calibration curves above-mentioned.

IV-4 Calculation of the Concentration Ratios

Then, each concentration ratio between $13CO_2$ and $^{12}CO_2$ is obtained. That is, the concentration ratio between $^{13}CO_2$ and $^{12}CO_2$ of the base gas is obtained by $^{13}Conc(B)/^{12}Conc(B)$, and the concentration ratio between $^{13}CO_2$ and $^{12}CO_2$ of the sample gas is obtained by $^{13}Conc(S)/^{12}Conc(S)$.

The concentration ratios may also be defined as $^{13}Conc(B)/(^{12}Conc(B)+^{13}Conc(B))$ and as $^{13}Conc(S)/(^{12}Conc(S)+^{13}Conc(S))$. Since the $^{12}CO_2$ concentrations are much greater than the $^{13}CO_2$ concentrations, the concentration ratios obtained by these different calculation methods are substantially equal to each other.

IV-5 Determination of $^{13}C$ Changed Portion

The $^{13}C$ changed portion in comparison of the sample gas data with the base gas data, is calculated by the following equation:

$$\Delta^{13}C = [\text{Sample Gas Concentration Ratio} - \text{Base Gas Concentration Ratio}] \times 10^3 / [\text{Base Gas Concentration Ratio}] \text{ (Unit: permil)}.$$

The invention claimed is:

1. In an isotope gas analysis in which gas to be measured or an expired breath of a human being containing, as gas components, carbon dioxide $^{13}CO_2$ and carbon dioxide $^{12}CO_2$, is introduced into a cell, and the intensities of transmitted lights having wavelengths suitable for measurement of the respective gas components, are measured and then data-processed to measure the concentration of the carbon dioxide $^{13}CO_2$, a gas injection amount determining method comprising the steps of:

filling the cell with the air at an atmospheric pressure;

operating a gas injection device so as to suck the air of a predetermined volume Va, the gas injection device being arranged to inject the gas to be measured into the cell;

transferring the air stored in the gas injection device into the cell to pressurize the cell inside, and measuring the cell inside pressure P; and subtracting the cell volume Vc from the product obtained by multiplying the sum V0 of the volume Va and the cell volume Vc, by the ratio P0/P in which P0 is the target pressure of the gas to be measured in isotope gas analysis measurement, thus determining the one-time gas injection amount of the gas injection device.

2. A gas injection amount determining method according to claim 1, wherein the cell volume Vc includes a net volume of the cell and volumes of pipes, valves, and a pressure sensor which are in connection through the cell.

3. A gas injection amount determining method according to claim 1 or claim 2, wherein the target pressure P0 of the gas to be measured is equal to the gas pressure at which a calibration curve for determining the relationship between absorbance and concentration of carbon dioxide $^{13}CO_2$, has been prepared.

4. In an isotope gas analyzing and measuring method in which gas to be measured or an expired breath of a human being containing, as gas components, carbon dioxide $^{13}CO_2$ and carbon dioxide $^{12}CO_2$, is introduced into a cell, and the intensities of transmitted lights having wavelengths suitable for measurement of the respective gas components, are measured and then data-processed to measure the concentration of the carbon dioxide $^{13}CO_2$, the isotope gas analyzing and measuring method comprising the steps of:

filling the cell with the air at an atmospheric pressure;

operating a gas injection device so as to suck the air of a predetermined volume Va, the gas injection device being arranged to inject the gas to be measured into the cell;

transferring the air stored in the gas injection device into the cell to pressurize the cell inside, and measuring the cell inside pressure P;

subtracting the cell volume Vc from the product obtained by multiplying the sum V0 of the volume Va and the cell volume Vc, by the ratio P0/P in which P0 is the target pressure of the gas to be measured in isotope gas analysis measurement, thus determining the one-time gas injection amount of the gas injection device; and collecting gas to be measured having the volume thus determined, by the gas injection device, transferring the gas thus collected, into the cell containing gas to be measured at an atmospheric pressure, thereby to pressurize the cell inside, and measuring the concentration of carbon dioxide $^{13}CO_2$ or the concentration ratio $^{13}CO_2/^{12}CO_2$.

5. An isotope gas analyzing and measuring method according to claim 4, wherein the cell volume Vc includes a net volume of the cell and volumes of pipes, valves and a pressure sensor which are in connection through the cell.

6. In an isotope gas analyzing and measuring apparatus in which gas to be measured or an expired breath of a human being containing, as gas components, carbon dioxide $^{13}CO_2$ and carbon dioxide $^{12}CO_2$, is introduced into a cell, and the intensities of transmitted lights having wavelengths suitable for measurement of the respective gas components, are measured and then data-processed to measure the concentration of the carbon dioxide $^{13}CO_2$, the isotope gas analyzing and measuring apparatus comprising:

a gas injection device for injecting gas into the cell;

gas transferring means for transferring the gas stored in the gas injection device into the cell;

a pressure sensor for measuring the pressure of the gas housed in the cell; and gas injection amount determining means arranged such that the air having a predetermined volume Va is sucked by the gas injection device, that the air stored in the gas injection device is transferred to the cell filled with the air at an atmospheric pressure, thereby to pressurize the cell inside, that the cell inside pressure P is measured, and that the cell volume Vc is subtracted from the product obtained by multiplying the sum V0 of the volume Va and the cell volume Vc, by the ratio P0/P in which P0 is the target pressure of the gas to be measured in isotope gas analysis measurement, thus determining the one-time gas injection amount of the gas injection device;

whereby gas to be measured having the volume determined by the gas injection amount determining means, is collected by the gas injection device, the gas thus collected is transferred into the cell filled with gas to be measured at an atmospheric pressure, and the concentration of carbon dioxide $^{13}CO_2$ or the concentration ratio $^{13}CO_2/^{12}CO_2$ is measured.

7. An isotope gas analyzing and measuring apparatus according to claim 6, wherein the cell volume Vc includes a net volume of the cell and volumes of pipes, valves and the pressure sensor which are in connection through the cell.

* * * * *